(12) United States Patent
Gutman et al.

(10) Patent No.: US 6,316,627 B1
(45) Date of Patent: Nov. 13, 2001

(54) PROCESS FOR THE PREPARATION OF FLECAINIDE

(75) Inventors: Arie L. Gutman, Haifa; Genady Nisnevich; Eleonora Shkolnik, both of Nesher; Igor Zaltzman; Boris Tishin, both of Haifa, all of (IL)

(73) Assignee: Fine Tech Ltd., Haifa (IL)

( * ) Notice: Subject to any disclaimer, the term of this patent is extended or adjusted under 35 U.S.C. 154(b) by 0 days.

(21) Appl. No.: 09/422,931

(22) Filed: Oct. 21, 1999

Related U.S. Application Data

(63) Continuation-in-part of application No. PCT/IL98/00315, filed on Jul. 7, 1998, and a continuation-in-part of application No. PCT/IL98/00187, filed on Apr. 20, 1998.

(30) Foreign Application Priority Data

Apr. 21, 1997 (IL) ....................................................... 120715
Jul. 11, 1997 (IL) ....................................................... 121288

(51) Int. Cl.$^7$ ..................... C07D 211/26; C07D 213/24; C07C 253/16; C07C 255/14
(52) U.S. Cl. .......................... 546/233; 558/311; 558/399; 546/337
(58) Field of Search .................................. 546/233, 234, 546/337; 558/311, 399

(56) References Cited

U.S. PATENT DOCUMENTS 4,952,574 * 8/1990 Banitt .................................... 514/315

FOREIGN PATENT DOCUMENTS 2 045 760 * 11/1980 (GB) ..................................... 546/233

OTHER PUBLICATIONS

Boyle, "270. Sur les esters actives I. Aminolyse des derives acyles des oximes et amidoximes", *Helvetica Chimica Acta*, vol. 47, No. 8, pp. 2444–2448, (1964).
Chemical Abstracts, Bibliographic Information.
Schwyzer et al, "Uber aktivierte Ester. I. Aktivierte Ester der Hippursaure und ihre Umsetzungen mit Benzylamin", *Helvetica Chimica Acta.*, vol. 38, No. 7–8, pp. 69–79, (1955).
Schwyzer et al., "Uber aktivierte Ester. II. Synthese aktivierte Ester von Aminosaure–Derivaten", *Helvetica Chimica Acta.*, vol. 38, No. 9, pp. 80–83, (1955).
Schwyzer et al., "Uber aktivierte Ester. III. Umsetzungen aktivierter Ester von Aminosauer–und Peptid–Derivaten mit Aminen und Aminosaureestern", *Helvetica Chimica Acta*, vol. 38, No. 9–10, pp. 83–91, (1955).
Abstract of JP 0539240.
J. Wrobel et al, "Syntheses of Tolrestat Analogues Containing Additional Substitutes in the Ring and Their Evaluation as Aldose Reductase Inhibitors. Identification of Potent, Orally Active 2–Fluoro Derivatives"; J. Med.Chem. 34, 8(1991), 2504–2520.

Flecainide, Merck Index, 12$^{th}$ edition, 4136, p. 694.

(List continued on next page.)

*Primary Examiner*—C. S. Aulakh
(74) *Attorney, Agent, or Firm*—Needle & Rosenberg, PC

(57) ABSTRACT

A process for the preparation of trifluoroethoxy benzoic acid derivatives, in particular Flecainide, and their pharmaceutically acceptable salts, starting with commercially available halobenzoic acids and involving the use of simple reagents and low cost solvents, to afford high overall yield of the product.

The above object is achieved in accordance with the present invention which, in one aspect thereof, provides a process for preparing a compound of formula (A):

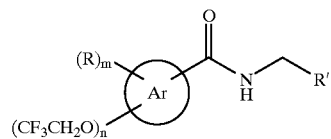

(A)

and pharmaceutically acceptable salts thereof, which process comprises the steps of:

a) reacting a halobenzoic acid or a salt thereof of the formula [II]

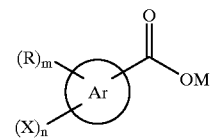

[II]

with 2,2,2-trifluoroethanol in the presence of a strong base and a copper containing material, if desired followed by acidification to obtain a compound of formula [I]

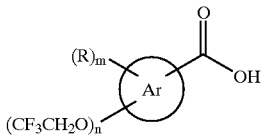

[I]

b) converting the product obtained in step a) above into the compound of formula (A) or a pharmaceutically acceptable salt thereof.

21 Claims, No Drawings

OTHER PUBLICATIONS

Banitt et al, "Antiarrhythmics, N–(Aminoalkylene)trifluoroethoxybenzamides and N–Aminoalkyele, trifluoroethoxynapthamides", *J. Med Chem* 18(11):1130–1134 (1975).

Banitt et al, "Antiarrhythmics. 2. Synthesis and Antiarrhythmic Activity of N–(Piperidylalkyl)trifluoroethoxybenzamides", *J. Med Chem* 20(6):821–826 (1977).

R. Buyle, "Sur les esters actives I. Aminolyse des derives acyles des oximes et amidoximes", *Helvetica Chimica Acta*, 47:2444–2448 (1964).

*Chemical Abstract* 114:122069, Spanish Patent ES 2 007 802 to Rubio Zurito et al of Jul. 1, 1989.

* cited by examiner

PROCESS FOR THE PREPARATION OF FLECAINIDE

CROSS REFERENCE TO RELATED APPLICATIONS

This application is a continuation-in-part of copending patent application Nos. PCT/IL98/00187, filed on Apr. 20, 1998, and PCT/IL98/00315, filed on Jul. 7, 1998, the entire contents of each of which being hereby incorporated herein by reference.

FIELD OF THE INVENTION

The present invention relates to a novel process for the preparation of Flecainide or a precursor thereof, to a novel intermediate used in this process and its preparation.

BACKGROUND OF THE INVENTION

Flecainide [2,5-bis(2,2,2-trifluoroethoxy)-N-(2-piperidylmethyl)benzarnide] is an effective antiarrythnic drug that acts on the cell membrane to reduce fast inward depolarization current.

One prior art method for preparing Flecainide [IV], disclosed in British Patent Application No. 2,045,760, starts from 2,5-bis(2,2,2-trifluoroethoxy)benzoic acid [III].

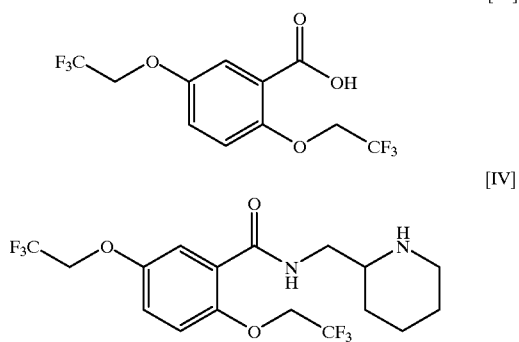

Compound [III] is prepared by a multi-stage process, comprising the conversion of 1,4dibromobenzene or hydroquinone to 1,4-bis(2,2,2-trifluoroethoxy)benzene, which is acetylated to form 2,5-bis(2,2,2-trifluoroethoxy) acetophenone. The acetophenone is then oxidized to form the corresponding benzoic acid derivative, which is then converted to its acid chloride and reacted either with 2-(aminomethyl)piperidine to form the Flecainide product in one step or with 2-(aminomethyl)pyridine, followed by catalytic hydrogenation of the pyridine ring, to form Flecainide in two steps.

The one step process has a serious disadvantage in that the acid chloride reacts non-selectively with both nitrogen atoms of the 2-(aminomethyl)piperidine, resulting in a mixture of the two acylated isomers. This is the main reason why the two-step process via the pyridine intermediate is commercially preferred, A further disadvantage is due to the fact that the acid chloride intermediate disclosed in GB 2,045,760A is a liquid which cannot be stored for long periods of time, but must be used immediately after it is prepared.

Trifluoroethoxybenzoic acids of the formula [I] are useful intermediates in the pharmaceutical industry.

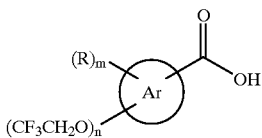

These compounds can be obtained by the reaction of hydroxybenzoic acids of the general formula [V] with 2,2,2-trifluoroethyl triflate [VI] according to Scheme 1 (Banift, E. H. etat., *J Med. Chem.* 18:1130 (1975)).

Scheme 1

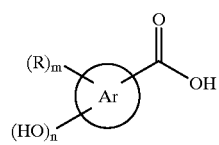

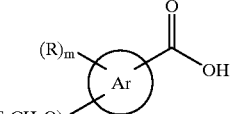

n is 1, 2 or 3.

This method requires the use of trifluoroethyl triflate [VI] which is costly and not easily available commercially.

Another method (GB 2045760A) involves the oxidation of the acetyl group of trifiuoroethoxyacetophenones with hypochlorite as shown in Scheme 2. However, partial halogenation of the benzene ring may occur in this process, thus making it difficult for production of the (2,2,2-trifluoroethoxy)benzoic acids [I] as pharmaceutical precursors.

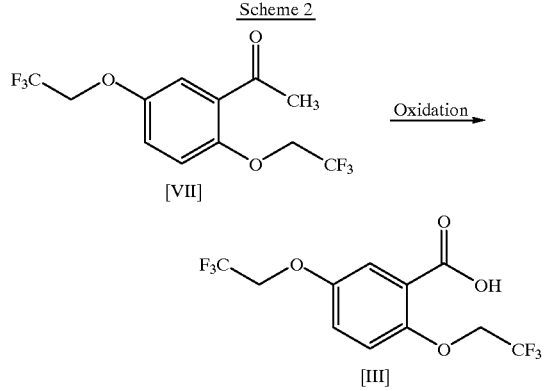

There is only one reported example of copper assisted fluoroalkoxy-de-halogenation of a 2-bromo-1-naphthalenecarboxylic acid derivative (Wrobel J. et al., J. Med. Chem. 34, 2504 (1991)). This example is very specific since it describes the de-halogenation of an active halogen, i.e. bromine, which is also located in a highly activated ortho position to a carboxylic group.

SUMMARY OF THE INVENTION

It is an object of the invention to provide a novel process for the preparation of trifluoroethoxy benzoic acid derivatives, in particular Flecainide, and their pharmaceutically acceptable salts, which is free of the above-mentioned disadvantages, staring with commercially available halobenzoic acids and involving the use of simple reagents and low cost solvents, to afford high overall yield of the product.

The above object is achieved in accordance with the present invention which, in one aspect thereof, provides a process for preparing a compound of formula (A):

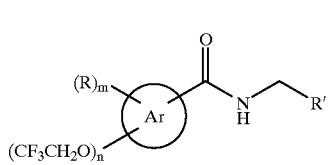
(A)

wherein
Ar represents a benzene ring;
R is hydrogen or a substituent selected from alkyl, alkoxy, alkylthio, halogen, haloalkyl, haloalkoxy, haloalkylthio, phenyl, phenoxy, benzyloxy, N-substitated or N,N-disubstituted amino groups, nitro, alkoxycarbonyl, cyano, carboxyl and when m>1 the R substituents may be the same or different;
R' is a 2-piperidyl or 2-pyridyl radical,
n is 1, 2or3;
m is 0, 1, 2, 3 or 4; where n+m≦5; and
pharmaceutically acceptable salts thereof, which process comprises the steps of:
a) reacting a halobenzoic acid or a salt thereof of the formula [II]

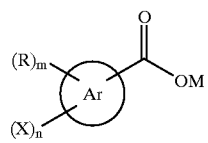
[II]

wherein
Ar, R, n and m are as defined above;
M is hydrogen or a metal, ammonium or phosphonium cation; and
X is Cl, Br or I, and when n >1 the X substituents may be the same or different;
with 2,2,2-trifluoroethanol in the presence of a strong base and a copper containing material, if desired followed by acidification to obtain a compound of formula [I]

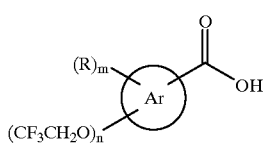
[I]

wherein
Ar, R, m and n are as defined above, and
b) converting the product obtained in step a) above into the compound of formula (A) or a pharmaceutically acceptable salt thereof.

According to a specific embodiment, the present invention provides a process for the preparation of a compound of formula (A'):

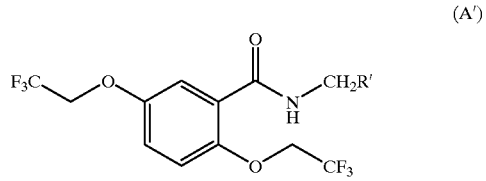
(A')

wherein
R' is a 2-piperidyl or 2-pyridyl radical, and pharmaceutically acceptable salts thereof.

Step b) above may be carried out by known procedures, such as those described in GB 2,045,760A or in Chem. Abs. 114:122069. Alternatively, according to a preferred embodiment, the present invention provides a novel process for step b). This novel process comprises:
(i) reacting a compound of formula [I] or a salt thereof, with a haloacetonitrile of the formula $XCH_2CN$, where X is Cl, Br or I, if necessary in the presence of an inorganic or organic base, to form the cyanomethyl ester of the formula:

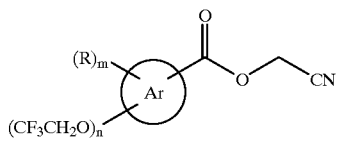

(ii) reacting the cyanomethyl ester with an amine of the formula $R'CH_2NH_2$ where R' is as defined above and, if desired,
(iii) converting the compound of the formula (A) into a pharmaceutically acceptable salt thereof.

Preferably, the halobenzoic acid in step a) is a compound of formula [XVII] or a salt thereof and the product of step a) is (2,2,2-trifluoroethoxy)-benzoic acid [III] or a salt thereof

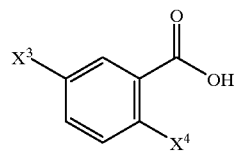
[XVII]

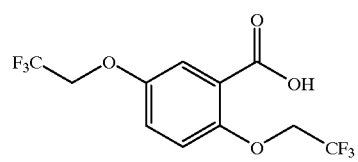
[III]

wherein:
$X^3$ is Br or I, $X^4$ is Cl, Br or I, or one of $X^3$ and $X^4$ may also be $CF_3CH_2O$—. (2,2,2-Trifluoroethoxy)benzoic acid [III] or a salt thereof may be converted in step b) into a compound of the formula (A') either by known methods or by the novel process of the present invention, which particularly comprises of:
(i) reacting 2,5-bis(2,2,2-trifluoroethoxy)benzoic acid [III] or a salt thereof, with a haloacetonitrile of the formula XCH$_2$CN, where X is Cl, Br or I, if necessary in the presence of an inorganic or organic base, to form the cyanomethyl ester of 2,5-bis(2,2,2-trifluoroethoxy) benzoic acid of the formula

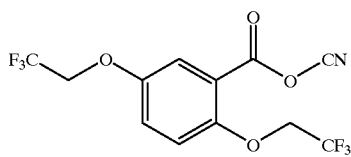

(ii) reacting the cyanomethyl ester with an amine of the formula R' CH$_2$NH$_2$ where R' is as defined above and, if desired, (iii) converting the resulting product of the formula (A')

(A')

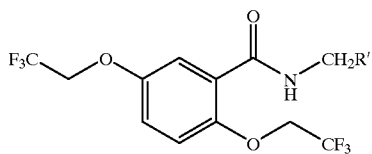

into a pharmaceutically acceptable salt thereof A' represents Flecainide when R' is 2-piperidyl.

In accordance with another aspect of this invention, there is provided the novel cyanomethyl ester of 2,5-bis(2,2,2-trifluoroethoxy)benzoic acid having the formula above. The novel intermediate of the present invention is a stable, solid comapound, obtainable in high yield, which can be easily purified by crystallization and stored for long periods of time.

DETAILED DESCRIPTION OF THE INVENTION (2,2,2-Trifluoroethoxy)benzoic acids [I] or salts thereof obtained in step a) of the process of the present invention may contain one or more is 2,2,2-trifluoroethoxy groups. Additionally, other substituents R as defined above may be present on the aromatic ring.

As defined herein, the term "halobenzoic acid" includes benzoic acids containing one or more halogen atoms and optionally additional substituents as defined for R above.

According to a preferred embodiment of the present invention, a chloro-, bromo- or iodo-benzoic acid is reacted with a metal trifluoroethoxide in the presence of copper iodide or bromide in an aprotic solvent Such aprotic solvent may be a dipolar aprotic solvent or an N-containing heterocycle or mixtures thereof Examples of dipolar aprotic solvents are N,N-dimnethylformnamide, N-methylpyrolidone, N,N-dimethylacetamide, DMSO and hexamethylphosphoramide. N-containing heterocyclic solvents used in the present invention are pyridine, picolines, lutidines, collidines, methylethylpyridine (MEP), other substituted pyridines, quinoline and substituted quinolines.

The reaction is preferably carried out at a temperature in the range of from ambient temperature to 170° C.

In the process of the invention, preferably at least one mole of 2,2,2-trifluoroethanol is used per each halogen atom of the halobenzoic acid [II] which is desired to be replaced by a trifluoroethoxy group. However, a large molar excess of 2,2,2-trifluoroethanol can be used in which cases this reactant may also serve as a solvent. At least one mole of 2,2,2-trifluoroeffianol per mole of the strong base should be used and the mole ratio of the copper containing compound to the halobenzoic acid [II] can be in the range of 0.01 to 2:1.

Suitable copper containing materials are for example: copper salts, copper oxides, metallic copper, copper alloys, etc.

Compounds of formula [I] are converted in step b) into a desired compound of formula (A) either by known procedures or by a novel process which constitutes a further aspect of the present invention.

According to one prior art method described in GB 2,045,760A, 1,4-bis(2,2,2-trifluoroethoxy)benzene is acetylated to form the corresponding acetophenone, which is then oxidized to the benzoic acid derivative. The benzoic acid derivative is converted into the acid chloride and reacted or with 2-(aminomethyl)pyridine, followed by catalytic hydrogenation of the pyridine ring, to form Flecainide in two steps.

According to another prior art method described in Chem. Abs. 114:122069, 2,5-bis(2,2,2-trifluoroethoxy)benzoic acid may be converted into the corresponding acid chloride, which is reacted with 2-azaindolizidine to give the heterocyclic amide [XX] as the HCl salt, which is hydrolized with aq. HCl in EtOH to give.

[XX]

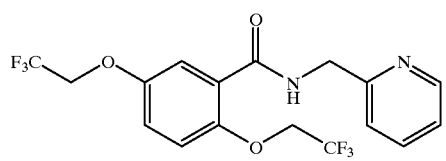

Alternatively, as mentioned above, step b) is carried out by a novel process which comprises:

(i) reacting a compound of formula [I] or a salt thereof, with a haloacetonitrile of the formula XCH$_2$CN, where X is Cl, Br or I, if necessary in the presence of an inorganic or organic base, to form the cyanomethyl ester of the formula:

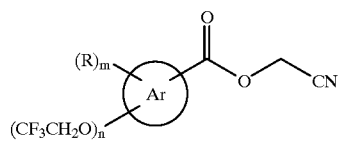

(ii) reacting the cyanomethyl ester with an amine of the formula R'CH2NH$_2$ where R' is as defined above and, if desired, (iii) converting the compound of the formula (A) into a pharmaceutically acceptable salt thereof.

Preferably, (2,2,2-trifluoroethoxy)benzoic acid [III] or a salt thereof is obtained in step a) of the process of the invention form a halobenzoic acid of the formula [XVII] and is subsequently reacted with a haloacetonitrile of the formula XCH$_2$CN wherein X is Cl, Br or I, preferably Cl, in the presence of an inorganic or organic base, to give at the end of the process a compound of formula (A').

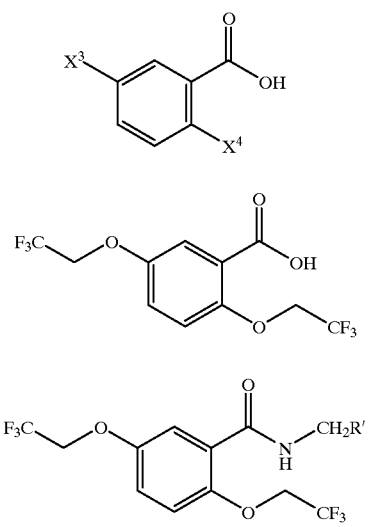

In the above formulae, $X^3$ is Br or I, $X^4$ is Cl, Br or I, or one of $X^3$ and $X^4$ may also be $CF_3CH_2O$—; R' is a 2-piperidyl or 2-pyridyl radical. When R' is 2-piperidyl, then the product is Flecainide or a salt thereof.

It was shown by Schwyzer et al. (Helvetica Chimica Acta, 1955, v. 38,69; 80;83) that cyanomethyl esters of aliphatic amino acids react selectively with primary amino groups. R. Buyle in Helvetica Chimica Acta, 1964, v. 47, p. 2444, showed that benzylamine reacts with cyanomethyl benzoate considerably slower than with cyanomethyl acetate. The present invention is based on the unexpected finding that 2,5-bis(2,2,2-trifluoroethoxy)benzoic acid activated by conversion to its cyanomethyl ester may react selectively and with high yield with primary amino groups of amines of the formula $R'CH_2NH_2$.

Thus, in step b) of the process, the cyanomethyl ester is reacted with an lo amine of the formula $R'CH_2NH_2$, where R' is as defined above, optionally in a suitable, inert solvent. Preferably, the reaction may be carried out by mixing together 2-(aminomethyl)piperidine with the cyanomethyl ester in a solvent such as 1,2-dimethoxyethane or ethyl acetate, to yield Flecainide (I) in a high yield.

The optional conversion of Flecainide into a pharmaceutically acceptable salt such as the acetate salt, is carried out by conventional methods.

The present invention will be described in more detail with the aid of the following non-limiting examples.

EXAMPLE 1

Synthesis of 2,5-bis(2,2,2-trifluoroethoxy)benzoic acid [III] from 5-bromo-2-chlorobenzoic acid [VIII] and 2,2,2-trifluoroethanol.

Scheme 3

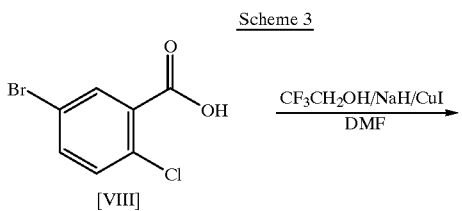

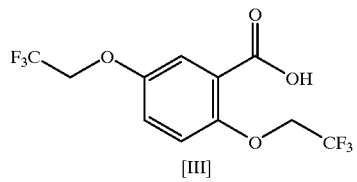

A 1 L round-bottomed flask equipped with a magnetic stirrer, a thermometer pocket, dropping funnel and a reflux condenser, was charged with 51.0 g of a 60% strength suspension of sodium hydride in mineral oil (equivalent to a total of 30.6 g (1.28 mole) of pure NaH) and 570 mL of anhydrous N,N-dimethylformamide. The mixture was cooled to room temperature in an ice-water bath and 189.5 g (1.90 mole) of anhydrous 2,2,2-trifluoroethanol were added dropwise during 40 minutes.

The mixture was cooled to room temperature and 24.8 g (0.13 mole) of anhydrous copper iodide and 59.5 g (0.25 mole) of 5-bromo-2-chlorobenzoic acid were added. The black reaction mixture was heated to about 110–115° C. and kept at this temperature for 2 hours.

The reaction mixture was cooled to room temperature and poured into a mixture of crushed ice (3 kg) and conc. hydrochloric acid (0.78 L). The mixture was vigorously stirred for 1 hour, the black precipitate was filtered off and washed at once with 200 mL of water. The obtained solid was suspended at room temperature in 1 L of 5% aqueous KOH under vigorous stirring for 15 min, followed by filtration through a Celite modified filter and washing with 100 mL of 5% aqueous KOH.

The transparent clear alkaline solution was thrice extracted with 150 mL of dichloromethane. The alkaline solution was added dropwise under vigorous stirring to mixture of 0.6 kg of ice and 0.2 L of conc. hydrochloric acid, at a temperature not higher than 0° C. and a pH 1. The mixture was stirred for 0.5 hours at these conditions. The obtained precipitate was filtered off, washed with water, collected and dried under vacuum to a constant weight. Yield: 64.7 g (81.4%) of crude 2,5-bis(2,2,2-trifluoroethoxy) benzoic acid, m.p. 116–118° C. After recrystallisation from an ethanol/water system, a product with m.p. 120–121° C. was obtained.

EXAMPLES 2 to 6

Syntheses of (2,2,2-trifluoroethoxy)benzoic acids of the general formula [X] by reacting sodium 2,2,2-trifluoroethoxide with corresponding halobenzoic acids [X] identified in Table 1.

The procedures set forth in Example 1 were followed with the exceptions apparent from Table 1. Sodium 2,2,2-trifluoroethoxide was prepared in situ by the action of sodium hydride on 2,2,2-trifluoroethanol.

In the following examples N,N-dimethylformamide, N,N-dimethylacetamide or N-methylpyrrolidone were used as solvents. In example 5, the solvent was 2,4,6-collidine. CuX was selected from copper iodide or copper bromide. The synthesis is described in Scheme 4.

Phisico-chemical parameters of 2,2,2-trifluoroethyl esters obtained by esterification of the products of experiments 2,3,4 and 1 are identical to corresponding 2,2,2-trifluoroethyl-2,5-bis(2,2,2-trifluoroethoxy)benzoates known in the art.

Scheme 4

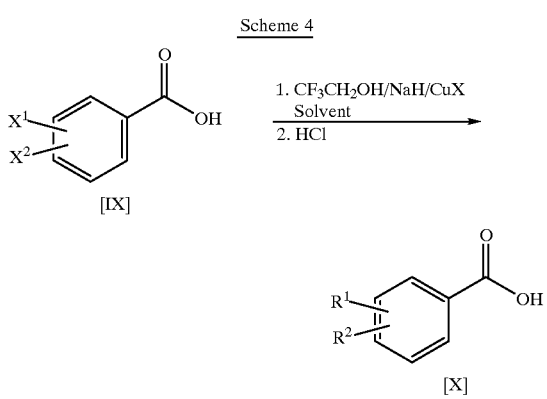

The results and the conditions are summarized in Table 1.

TABLE 1

| EXAMPLE NO. | $X^1$ | $X^2$ | $R^2$ | $R^3$ |
|---|---|---|---|---|
| 2 | 5-Br | 2-Br | 5-$CF_3CH_2O$ | 2-$CF_3CH_2O$ |
| 3 | 5-Br | 2-$CF_3CH_2O$ | 5-$CF_3CH_2O$ | 2-$CF_3CH_2O$ |
| 4 | 5-I | 2-Cl | 5-$CF_3CH_2O$ | 2-$CF_3CH_2O$ |
| 5 | 5-Cl | 2-Cl | 5-Cl | 2-$CF_3CH_2O$ |
| 6 | 5-$NO_2$ | 2-Cl | 5-$NO_2$ | 2-$CF_3CH_2O$ |

EXAMPLE 7

Synthesis of cyanomethyl ester of 2,5-bis(2,2,2-trifluoroethoxy)benzoic acid

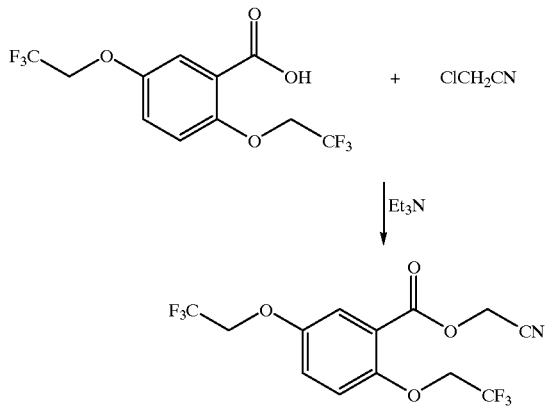

A 1 L two-neck round-bottomed flask equipped with a heating mantle, a magnetic stirrer and a reflux condenser was charged under argon with a mixture of 62.8 g (197.4 mmole) of 2,5-bis(2,2,2,-trifluoroethoxy)benzoic acid, 22.4 g (296.1 mmole) of chloroacetonitrile and 29.9 g (296.1 mmole) of lo triethylamine in 250 mL ethyl acetate (EtOAc). The obtained mixture was refluxed for 3 hours. After cooling to 10° C., the mixture was filtered through a column containing 50 g of silica gel to remove the formed trimethylammonium chloride. The filtrate was evaporated in vacuo and the product was dried under high vacuum for 1 hour at 50° C. The resulting colourless solidified oil was stirred with 200 mL of cold hexane to obtain white crystals. The crystals were filtered off, washed with cold hexane and dried at reduced pressure to give 60.0 g (85% yield) of cyanomethyl ester, having a purity of 99.5% (GC), m.p. 50–51° C., one spot on TLC.

1H NMR ($CDCl_3$) δ4.37 (4H,m); 4.93 (2H,s); 7.00 (1H,d); 7.17 (1H,dd); 7.44 (1H,d); HRMS:$M^+$ 357.0433, $C_{13}H_9NO_4F_6$.

EXAMPLE 8

Synthesis of Flecainide from the cyanomethyl ester of 2,5-bis (2,2,-2-trifluoroethoxy)benoic acid and 2-(aminomethyl)piperidine

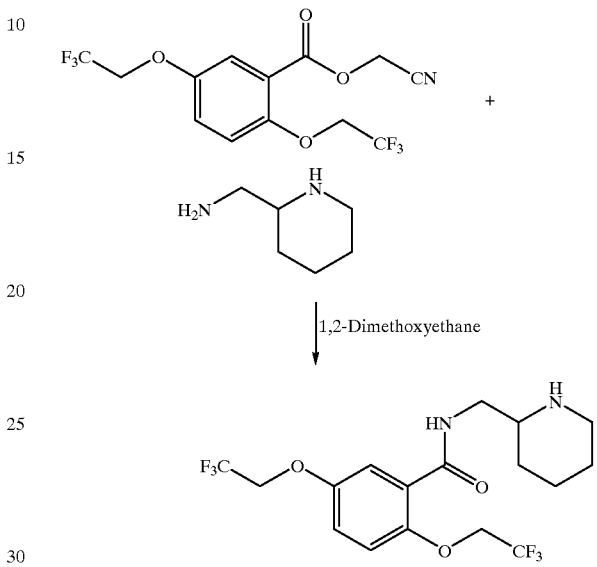

A mixture of the cyanomethyl ester prepared in Example 7 above (2.1 g, 5.9 mmole) and 2-(aminomethyl)piperidine (0.8 g, 7 mmole) in 1,2-dimethoxyethane (10 mL) was charged under argon into a 50 mL round-bottomed flask equipped with a magnetic stirrer. After stirring for 2.5 hours at room temperature, additional 2-(aminomethyl)piperidine (0.5 g, 4.7 mmole) was added. The mixture was stirred for additional 24 hours at room temperature. The solvent was removed in vacuo and the residue was dissolved in 10 mL methylene chloride. The obtained solution was extracted with water and the aqueous layer was extracted with additional 5 mL of methylene chloride. The combined organic layers were dried over sodium sulfate and evaporated under reduced pressure to give 1.9 g (77.6 yield) of white crystals of Flecainide, purity 99.1% (GC).

EXAMPLE 9

Synthesis of Flecainide acetate

A mixture of the cyanomethyl ester prepared in Example 7 (95.0 g. 0.27 mole) and 2-(aminomethyl) piperidine (35.4 g. 0.31 mole) in 450 mL ethyl acetate (max water content: 0.05%) was charged under argon into a 1 L round-bottom flask equipped with a dropping funnel and magnetic stirrer. After stirring for 2 hours at room temperature, the additional amount (24.2 g. 0.21 mole) of 2-(aminomethyl)piperidine was added, and the mixture was stirred for an additional period of 12 hours at room temperature.

The solvent was evaporated under reduced pressure. The residue was dissolved in 250 mnL. of dichloromethane. The obtained solution was treated with water (3×50 mL), dried with anhydrous $Na_2SO_4$ filtered and concentrated under reduced pressure.

The residue was dissolved in boiling ethyl acetate (800 mL), and 30 g (0.5 mole) of glacial acetic acetic acid was added dropwise to the obtained solution. The mixture was stirred under reflux for an additional 10 minutes and allowed to cool to room temperature overnight, followed by cooling into an ice bath for 4 hours. The crystalline product was filtered off, washed with cooled to 0° C. ethyl acetate (2×100 mL) and dried at 50° C. under reduced pressure, to obtain 103.0 g (82% from theoretical yield) of Flecainide acetate, m.p. 147–148° C.

EXAMPLE 10

Synthesis of 2,5-bis(2,2,2-trifluoroethoxy)-N-(2-pyriedysmethyl) benzamide

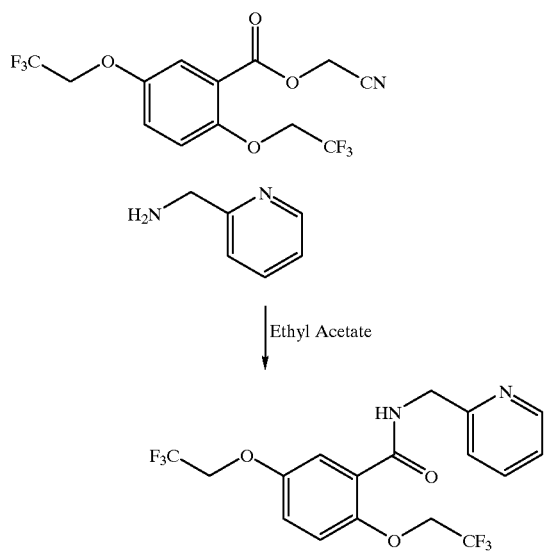

To a solution of 8.93 g (2.5 mmmole) of the cyanomethyl ester prepared in Example 7 in 80 mL of ethyl acetate under argon, 2-(aminomethyl)pyridine (3.2 g, 3.0 mmole) were added with stirring and the mixture was refluxed for 4 hours. An additional 1 g of 2-(aminomethyl)pyridine was added and the mixture was refluxed for two more hours. The ethyl acetate was evaporated under reduced pressure, and the residue was passed through a 12 cm column containing silica gel with a mixture of methylene chloride: hexane (1:1) as eluent. The column was washed with methylene chloride and the combined solutions were evaporated under reduced pressure. The residue was crystallized from $CH_2Cl_2$: hexane (1:2) to give 7 g (69% yield) of 2,5-bis(2,2,2-trifluoroethoxy)-N-(2-pyridylmethyl)benzanide m.p. 104–106° C., purity 99.8% (GC).

What is claimed is:

1. A process for preparing a compound of formula (A):

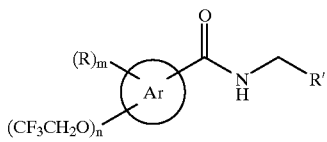

wherein

Ar represents a benzene ring;

R is hydrogen or a substituent selected from alkyl, alkoxy, alkylthio, halogen, haloalkyl, haloalkoxy, haloalkylthio, phenyl, phenoxy, benzyloxy, N-substituted or N,N-disubstituted amino groups, nitro, alkoxycarbonyl, cyano, carboxyl and when m>1 the R substituents may be the same or different;

R' is a 2-piperidyl or 2-pyridyl radical, n is 1, 2 or 3;

m is 0, 1, 2, 3 or 4; where n+m≦5; and pharmaceutically acceptable salts thereof, which process comprises the steps of:

a) reacting a halobenzoic acid or a salt thereof of the formula [II]

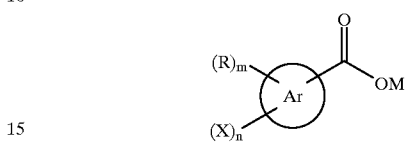

wherein

Ar, R, n and m are as defined above;

M is hydrogen or a metal, ammonium or phosphonium cation; and

X is Cl, Br or I, and when n>1 the X substituents may be the same or different;

with 2,2,2-trifluoroethanol in the presence of a strong base and copper or a copper compound or alloy, if desired followed by acidification to obtain a compound of formula [I]

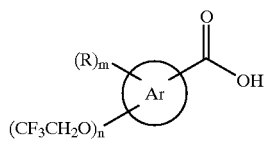

wherein Ar, R, m and n are as defined above, and b) converting the product obtained in step a) above into the compound of formula (A) or a pharmaceutically acceptable salt thereof.

2. The process of claim 1, wherein in step a) the reaction is carried out in the presence at least one of copper iodide and/or copper bromide.

3. The process of claim 1, wherein in step a) 2,2,2-trifluoroethanol is reacted with a strong base to form a 2,2,2-trifluoroethoxide and the product is reacted with a halobenzoic acid or salt thereof of formula [II] in the presence of copper or a copper compound or alloy.

4. The process of claim 1 wherein in step a) the reaction is conducted in an aprotic solvent.

5. The process of claim 4 wherein said aprotic solvent is a dipolar aprotic solvent or an N-containing heterocycle or mixtures thereof.

6. The process of claim 5 wherein the dipolar aprotic solvent is selected from N,N-dimethylformamide, N-methylpyrrolidone, N,N-dimethyl-acetamide, DMSO, hexamethylphosphoramide and mixtures thereof.

7. The process of claim 5 wherein the N-containing heterocycle is selected from pyridine, picolines, lutidines, collidines, methylethylpyridine (MEP), other substituted pyridines, quinoline and substituted quinolines.

8. The process of claim 1 wherein in step a) the strong base is selected from Na, NaH, $NaNH_2$, Na- and K-alkoxides, NaOH, KOH, fully N-substituted amidines, guauidines and tetraalkylammonium hydroxides and alcoxides.

9. A process according to claim 1 wherein step b) is carried out by:
(i) reacting a compound of formula [I] or a salt thereof, with a haloacetonitrile of the formula XCH$_2$CN, where X is Cl, Br or I, if necessary in the presence of an inorganic or organic base, to form the cyanomethyl ester of the formula:

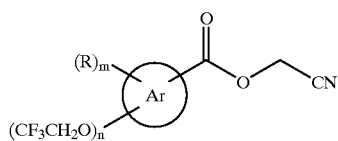

(ii) reacting the cyanomethyl ester with an amine of the formula R' CH$_2$NH$_2$ where R' is as defined above and, if desired,
(iii) converting the compound of the formula (A) into a pharmaceutically acceptable salt thereof.

10. The process of claim 1 wherein in step a) said halobenzoic acid is a compound of formula [XVII] or a salt thereof and said product is (2,2,2-trifluoroethoxy)benzoic acid of formula [III ] or a salt thereof

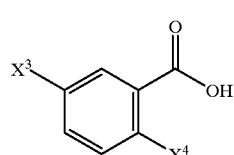

[XVII]

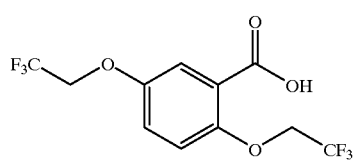

[III]

wherein:
X$^3$ is Br or I, X$^4$ is Cl, Br or I, or one of X$^3$ and X$^4$ may also be CF$_3$CH$_2$O—.

11. The process according to claim 10 wherein step b) is carried out by:
(i) reacting 2,5-bis(2,2,2-trifluoroethoxy)benzoic acid [III] or a salt thereof, with a haloacetonitrile of the formula XCH$_2$CN, where X is Cl, Br or I, if necessary in the presence of an inorganic or organic base, to form the cyanomethyl ester of the formula:

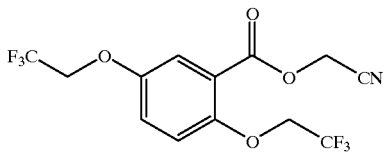

(ii) reacting the cyanomethyl ester with an amine of the formula R' CH$_2$NH$_2$ where R' is as defined in claim 1 and, if desired,
(iii) converting the resulting product of the formula (A')

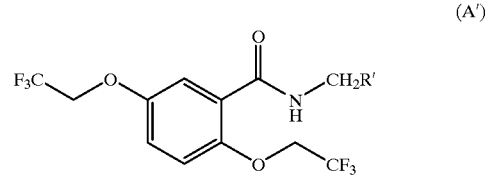

(A')

into a pharmaceutically acceptable salt thereof.

12. The process according to claim 9 or 11, wherein the reactions in steps i) and/or ii) and/or iii) are carried out in a suitable inert solvent.

13. The process according to claim 12, wherein ethyl acetate is used as the solvent in steps i) and/or ii), and/or iii).

14. The process according to claim 11, wherein the free 2,5-bis(2,2,2-trifluoroethoxy)benzoic acid is used as the starting material in step i) and the reaction is conducted in the presence of a base.

15. The process according to claim 9 or 14, wherein a tertiary amine is used in step i) as a base.

16. The process according to claim 15, wherein the tertiary amine is selected from triethylamine, diisopropylethylamine, N-ethylpiperidine.

17. The process according to claim 11, wherein R' is 2-piperidyl to obtain Flecainide.

18. The process according to claim 17, further comprising the conversion of the Flecainide product to its acetate.

19. Cyanomethyl ester of 2,5-bis(2,2,2-trifluoroethoxy) benzoic acid having the formula

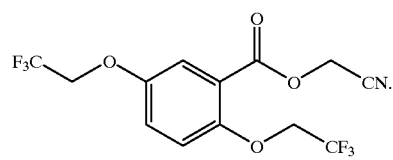

20. A process for the preparation of the cyanomethyl ester in claim 19, which comprises reacting 2,5-bis(2,2,2-trifluoroethoxy)benzoic acid or salt thereof, with a haloacetonitrile of the formula XCH$_2$CN wherein X is X$_b$Cl, Br, or I when m>1 the X substitutes may be the same or different and, if necessary, in the presence of an inorganic or organic base.

21. The process according to claim 20, carried out in a suitable inert solvent.

* * * * *

UNITED STATES PATENT AND TRADEMARK OFFICE
CERTIFICATE OF CORRECTION

PATENT NO. : 6,316,627 B1
DATED : November 13, 2001
INVENTOR(S) : Gutman et al.

It is certified that error appears in the above-identified patent and that said Letters Patent is hereby corrected as shown below:

Column 14,
Lines 50-66, claim 20 should be amended as follows:
20. A process for the preparation of the cyanomethyl ester in claim 19, which comprises reacting 2,5-bis(2,2,2-trifluoroethoxy)benzoic acid or a salt thereof, with a haloacetonitrile of the formula $XCH_2CN$ wherein X is [$X_b$] Cl, Br, or I [when M>1 the x substitutes may be the same or different ] and, if necessary, in the presence of an inorganic or organic base.

Signed and Sealed this

Fourteenth Day of May, 2002

Attest:

Attesting Officer

JAMES E. ROGAN
*Director of the United States Patent and Trademark Office*